(12) United States Patent
Nitzert et al.

(10) Patent No.: US 11,577,072 B2
(45) Date of Patent: Feb. 14, 2023

(54) METHODS AND DEVICES FOR THE ELECTRICAL STIMULATION OF BRAIN TISSUE VIA ELECTRODES WITHIN CRANIAL BONE

(71) Applicant: Precisis AG, Heidelberg (DE)

(72) Inventors: Michael Nitzert, Altoetting (DE); Jean Gotman, Westmount (CA); Gregor Remmert, Heidelberg (DE)

(73) Assignee: Precisis GmbH, Heidelberg (DE)

( * ) Notice: Subject to any disclaimer, the term of this patent is extended or adjusted under 35 U.S.C. 154(b) by 0 days.

(21) Appl. No.: 16/342,375

(22) PCT Filed: Jun. 23, 2017

(86) PCT No.: PCT/EP2017/065568
§ 371 (c)(1),
(2) Date: Apr. 16, 2019

(87) PCT Pub. No.: WO2018/072894
PCT Pub. Date: Apr. 26, 2018

(65) Prior Publication Data
US 2019/0240479 A1 Aug. 8, 2019

Related U.S. Application Data

(60) Provisional application No. 62/410,222, filed on Oct. 19, 2016.

(51) Int. Cl.
*A61N 1/36* (2006.01)
*A61N 1/05* (2006.01)
(Continued)

(52) U.S. Cl.
CPC .............. *A61N 1/0539* (2013.01); *A61B 5/24* (2021.01); *A61B 5/68* (2013.01); *A61B 5/6878* (2013.01);
(Continued)

(58) Field of Classification Search
CPC .............. A61N 1/0539; A61N 1/37514; A61N 1/36002; A61N 1/0529; A61N 1/3605;
(Continued)

(56) References Cited

U.S. PATENT DOCUMENTS

| 4,936,306 A | 6/1990 | Doty |
|---|---|---|
| 5,111,812 A | 5/1992 | Swanson et al. |

(Continued)

FOREIGN PATENT DOCUMENTS

| CA | 1219642 A | 3/1987 |
|---|---|---|
| JP | 2001-271203 A | 10/2001 |

(Continued)

OTHER PUBLICATIONS

International Preliminary Report on Patentability for International Patent Application No. PCT/US2005/037246, dated May 30, 2007 (7 pages).

(Continued)

*Primary Examiner* — Ahmed M Farah
(74) *Attorney, Agent, or Firm* — Clark & Elbing LLP

(57) ABSTRACT

The invention features methods and devices useful for stimulating brain tissue in a subject via electrodes within cranial bone. These methods and devices may be utilized for the detection, prevention, and/or treatment of neurological disorders via electric stimulation. Additionally, the methods and devices disclosed herein may be useful for the treatment, inhibition, and/or arrestment of the growth of tumors.

27 Claims, 8 Drawing Sheets

(51) Int. Cl.
  *A61N 1/375* (2006.01)
  *A61B 5/00* (2006.01)
  *A61B 5/24* (2021.01)
  *A61N 1/20* (2006.01)
  *A61N 1/378* (2006.01)
  *A61N 1/04* (2006.01)

(52) U.S. Cl.
  CPC ............. *A61N 1/0529* (2013.01); *A61N 1/20* (2013.01); *A61N 1/36002* (2017.08); *A61N 1/3605* (2013.01); *A61N 1/36153* (2013.01); *A61N 1/36157* (2013.01); *A61N 1/36175* (2013.01); *A61N 1/3756* (2013.01); *A61N 1/3787* (2013.01); *A61N 1/37514* (2017.08); *A61N 1/0456* (2013.01); *A61N 1/36025* (2013.01)

(58) Field of Classification Search
  CPC ............ A61N 1/36153; A61N 1/36157; A61N 1/36175; A61N 1/3756; A61N 1/0531; A61N 1/0534; A61N 1/36; A61N 1/3606; A61N 1/36146; A61N 1/36171; A61N 1/378; A61B 5/68; A61B 5/6878
  USPC .......................................... 607/2, 46, 58, 61
  See application file for complete search history.

(56) References Cited

U.S. PATENT DOCUMENTS

| | | | |
|---|---|---|---|
| 5,792,186 A | 8/1998 | Rise | |
| 5,873,898 A | 2/1999 | Hemming et al. | |
| 6,016,449 A | 1/2000 | Fischell et al. | |
| 7,006,859 B1 | 2/2006 | Osorio et al. | |
| 7,101,351 B2 | 9/2006 | Crawford et al. | |
| 7,221,981 B2 | 5/2007 | Gliner | |
| 7,305,268 B2 | 12/2007 | Gliner et al. | |
| 7,440,806 B1 * | 10/2008 | Whitehurst | A61M 5/14276 607/45 |
| 8,190,248 B2 | 5/2012 | Besio et al. | |
| 8,204,572 B1 | 6/2012 | Lang et al. | |
| 10,737,091 B2 * | 8/2020 | Remmert | A61N 1/0456 |
| 2002/0072770 A1 | 6/2002 | Pless | |
| 2003/0050673 A1 | 3/2003 | Yamazaki et al. | |
| 2003/0187490 A1 | 10/2003 | Gliner | |
| 2004/0102828 A1 | 5/2004 | Lowry et al. | |
| 2004/0153129 A1 | 8/2004 | Pless et al. | |
| 2004/0158298 A1 | 8/2004 | Gliner et al. | |
| 2004/0199237 A1 | 10/2004 | Mills et al. | |
| 2005/0070810 A1 | 3/2005 | Kennedy | |
| 2009/0112273 A1 | 4/2009 | Wingeier et al. | |
| 2009/0118804 A1 | 5/2009 | Moffitt et al. | |
| 2010/0114261 A1 * | 5/2010 | Errico | A61N 1/0519 607/2 |
| 2011/0137381 A1 | 6/2011 | Lee et al. | |
| 2011/0301665 A1 * | 12/2011 | Mercanzini | A61B 5/6868 607/45 |
| 2012/0277834 A1 * | 11/2012 | Mercanzini | A61N 1/36125 607/116 |
| 2016/0129246 A1 * | 5/2016 | Housley | A61K 38/185 604/20 |
| 2018/0015286 A1 * | 1/2018 | Liedler | A61N 1/36175 |
| 2020/0188660 A1 * | 6/2020 | Franke | A61B 5/1107 |
| 2020/0330749 A1 * | 10/2020 | Gribetz | A61N 1/37514 |
| 2022/0001182 A1 * | 1/2022 | Eskuri | A61N 1/0529 |

FOREIGN PATENT DOCUMENTS

| | | |
|---|---|---|
| WO | WO-03/089057 A1 | 10/2003 |
| WO | WO-2011/067297 A1 | 6/2011 |
| WO | WO-2013/018088 A1 | 2/2013 |
| WO | WO-2015/021075 A1 | 2/2015 |

OTHER PUBLICATIONS

Extended European Search Report for European Patent Application No. 05808963.2, dated May 11, 2010 (6 pages).

International Search Report and Written Opinion for International Application No. PCT/EP2017/065568, dated Sep. 6, 2017 (17 pages).

* cited by examiner l/d = 0.3-0.5

METHODS AND DEVICES FOR THE ELECTRICAL STIMULATION OF BRAIN TISSUE VIA ELECTRODES WITHIN CRANIAL BONE

FIELD OF THE INVENTION

The invention features devices and methods for the electrical stimulation of brain tissue in subjects.

BACKGROUND

Electrical stimulation of neural or nervous tissue, e.g., brain tissue, is a well-established procedure for the treatment of various neurological disorders. Electrical stimulation has been successfully applied to treat diseases, such as epilepsy, migraine, stroke, and many other neurological illnesses or conditions. Currently available electrical stimulation techniques, such as Deep Brain Stimulation (DBS) and Responsive Neuro Stimulation (RNS), require implantation of the devices into the brain and are very invasive to the patient. In contrast, transcranial stimulation devices, such as transcranial direct current stimulation (tDCS) or transcranial magnetic stimulation (TMS), are non-invasive treatment methods, but are limited to hospital use as inpatient devices. For instance, TMS devices must be stationary in hospitals and are not mobile or implantable because of the large current source required to induce an effective electrical field in the brain when the coil is located outside the head.

tDCS is a non-invasive electrical stimulation technique which involves the steady application of direct current on the surface of the scalp via electrodes. The therapeutic effect of tDCS is thought to result from local modulations of electrical potential outside of neural cells, which depolarizes or hyperpolarizes the neural resting membrane potential, and thus, alters action potential formation. The underlying physiological basis for tDCS is likely due to the long-term changes in the excitability of neural cells, i.e., neuroplasticity, after the stimulation ends. The duration of neural changes is dependent on both the length and intensity of electrical stimulation. Previous studies have shown that anodal (e.g., positively charged) tDCS stimulation depolarizes resting membrane potential, resulting in an increase in neuronal excitability and more spontaneous cell firing. In contrast, cathodal (e.g., negatively charged) tDCS stimulation hyperpolarizes resting membrane potential, resulting in a concomitant decrease in neuronal excitability and spontaneous cell firing.

Studies have revealed that anodal tDCS of the prefrontal cortex enhances the implicit learning capability and improves working memory in treated patients. Cathodal tDCS has also been shown to be effective for the treatment of refractory epilepsy. Furthermore, tDCS stimulation of the prefrontal dorso-lateral cortex was shown to significantly reduce the symptoms of depression in treated subjects. Thus, tDCS is considered a safe, non-invasive treatment for a variety of neurological disorders, which has relatively few side effects and is more effective than treatment with TMS due to the longer duration of change in cortex excitability. Notably, treatment with tDCS is rarely implemented outside of the hospital setting due to the lack of accessible and safe devices for therapeutic purposes.

Electrical stimulation from locations outside the cranium is difficult due to the relatively low electrical conductivity of the cranial bone, resulting in greater power requirements for extracranial devices than electrodes implanted within the cranium. Therefore, extracranial devices require higher current to achieve the appropriate current density within the targeted brain tissue area. Currently, there is a lack of electrostimulation devices available that are both effective and accessible to patients with reduced space, power, and current requirements than extracranial devices.

SUMMARY OF THE INVENTION

The present invention features devices for the electrical stimulation of brain tissue and/or the detection of brain activities in subjects (e.g., mammals, such as humans) via electrodes within the cranial bone. In particular, the structural design of the electrostimulation devices of the invention allows for stimulating electrodes that are configured for implantation in cranial bone. The electrodes of the invention are less invasive and have reduced space and power requirements relative to extracranial devices.

In addition to one or more stimulation electrodes, the electrostimulation devices can include, e.g., a control module operatively coupled to a power supply and a stimulation sub-system controlled by the control module to deliver electrical stimulation to selected brain areas. The control module may include a subsystem operatively coupling the control module to one or more electrodes (e.g., one, two, three, four, five, or six or more electrodes). In particular the control module may include a subsystem operatively coupling the control module to a single electrode. Alternatively, the control module may include a subsystem operatively coupling the control module to the plurality of stimulating electrodes, such as a plurality of electrodes implanted to cover a large brain region in, e.g., a Laplacian electrode configuration. For instance, the control module may select stimulating electrodes among the plurality of stimulating electrodes in order to switch selected electrodes between different patterns without altering the placement of the plurality of stimulating electrodes in the patient's cranium. The control module can further include a responsive analysis subsystem for analyzing electrical activity within the brain and/or a detection subsystem for detecting abnormal (e.g., harmful) electrical activity within the brain of the patient.

A first aspect of the invention features an electrostimulation device including a power source (e.g., a wireless power source) electrically coupled to a component including at least one electrode composed of one or more materials that promote osteoblast adhesion, such as high purity titanium, a titanium alloy (e.g., Ti-6Al-4V, Ti-6Al-7Nb, or Ti-13Nb-13Zr), aluminum oxide (e.g., monocrystalline aluminum oxide or polycrystalline aluminum oxide), bioactive glass, hydroxyapatite, a ceramic-coated metal (e.g. titanium, gold, platinum, or iridium), calcium phosphate, cobalt-chromium, zirconium oxide, barium aluminate, barium titanate, iron oxide, and zinc oxide. In particular, the at least one electrode has a cylindrical or slightly conical shape including a first side and a second side, such as the at least one electrode is configured to be positioned in cranial bone with the first side proximate to an outer surface of the cranial bone and the second side proximate to an inner surface of the cranial bone (e.g., about 0.1 mm to about 8 mm from the inner surface of the cranial bone). The at least one electrode is characterized by a cylinder length to diameter (l/d) ratio of about 0.3 to about 5.0, about 0.3 to about 2.0, or about 0.3 to about 0.5 (e.g., a l/d ratio of about 0.3, about 0.5, about 0.7, about 0.9, about 1.1, about 1.3, about 1.5, about 1.7, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8, or about 5) and/or a surface roughness (Sa) of about 0.5 µm to about 3.0 µm (e.g., about 0.5 µm, about 1.0 µm, about 1.5 µm, about 2.0 µm, about 2.5 µm, or about 3.0 µm) on the second side of the at least one electrode. In particular embodiments, the l/d ratio is about 0.3 to about 0.5.

In some embodiments, the Sa is about 1.0 µm to about 2.0 µm on the second side of the at least one electrode (e.g., about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, or about 2.0 µm on the second side of the at least one electrode). For example, the Sa can be achieved by sandblasting, acid etching, anodic oxidation, laser modification, and/or plasma coating.

In some embodiments, the electrostimulation device further includes threads, such as self-cutting, single-start, or multiple-start threads. Preferably the threads are bone-condensing threads, such as buttress threads. The threads can include one or more insulating materials, such as silicone, plastic, rubber, ceramic, or glass.

In various embodiments, the component of the electrostimulation device can further include a counter electrode. In particular, the counter electrode is separated from the at least one electrode with one or more insulating materials, such as silicone, plastic, rubber, ceramic, or glass. For example, the at least one electrode and the counter electrode are connected by one or more electric leads.

In some embodiments, the component of the electrostimulation device can further include one or more electrically conductive materials (e.g., a conductive cement or paste) in contact with the first side of the at least one electrode. Additionally, the first side of the at least one electrode can include one or more insulating materials (e.g., a non-conductive bone cement, ceramic, or paste). Moreover, the at least one electrode, particularly the second side of the at least one electrode, can include one or more materials optimized for a high charge injection capacity, such as iridium oxide, platinum oxide, platinum-iridium alloy, or titanium nitride.

In various embodiments, the device further includes a control module operatively coupled to the power supply and a stimulation sub-system controlled by the control module. The component of the electrostimulation device can further include an external abutment on the first side of the at least one electrode. For example, the abutment is connected to a compartment of the at least one electrode including the power source.

In preferred embodiments, the component of the electrostimulation device has a diameter of about 4 mm to about 12 mm (e.g., about 4 mm to about 10 mm, about 6 mm to about 12 mm, about 8 mm to about 11 mm, about 4 mm to about 9 mm, about 6 mm to about 8 mm, about 10 mm to about 12 mm, about 4 mm to about 5 mm, about 4 mm to about 12 mm, about 5 mm to about 8 mm, about 6 mm to about 9 mm, or about 9 mm to about 12 mm).

In preferred embodiments, the power source is a wireless power source. For example, the device includes a compartment including the wireless power source. In particular, the compartment further includes a control module operatively coupled to the wireless power source, in which the control module further includes an analysis sub-system. For instance, the power source includes a rechargeable battery.

In some embodiments, the electrostimulation device can include a plurality of electrodes. For instance, the device further includes a switching sub-system. Preferably, the electrostimulation device is configured for implantation in cranial bone of a patient (e.g., a human).

A second aspect of the invention features a method for stimulating brain tissue in a subject (e.g., a human) using the electrostimulation device of the first aspect of the invention. The method includes: (i) positioning the at least one electrode within cranial bone, in which the first side of the at least one electrode is proximate to an outer surface of the cranial bone and the second side of the at least one electrode is proximate to an inner surface of the cranial bone, in which the second side is configured to be positioned about 0.1 mm to about 8 mm from the inner surface of the cranial bone, and in which the inner surface of the cranial bone defines, in part, a space containing brain tissue; and (ii) delivering electrical stimulation to the brain tissue in the space. In particular, the second side of the at least one electrode is positioned about 2 mm to about 8 mm, about 1 mm to about 4 mm, or about 0.5 mm to about 2 mm from the inner surface of the cranial bone, such as about 0.1 mm to about 8 mm, about 2 mm to about 8 mm, about 4 mm to about 8 mm, about 0.1 mm to about 2 mm, about 2 mm to about 6 mm, about 2 mm to about 4 mm, or about 4 mm to about 6 mm from the inner surface of the cranial bone (e.g., 0.1, 0.2±0.1, 0.4±0.1, 0.6±0.1, 0.8±0.1, 1±0.5, 2±0.5, 3±0.5, 4±0.5, 5±0.5, 6±0.5, 7±0.5, or 8±0.5 mm from the inner surface of the cranial bone).

A third aspect of the invention features a method for stimulating brain tissue in a subject that includes a first step of providing an electrostimulation device including a power source electrically coupled to a component including at least one electrode; a second step of positioning at least a portion of the at least one electrode within cranial bone; and a third step of delivering electrical stimulation to the brain tissue in the space. The at least one electrode includes a first side coupled to a power source and proximate to an outer surface of the cranial bone, and a second side proximate to an inner surface of the cranial bone, in which the second side is configured to be positioned about 0.1 mm to about 8 mm, about 2 mm to about 8 mm, about 4 mm to about 8 mm, about 0.1 mm to about 2 mm, about 2 mm to about 6 mm, about 2 mm to about 4 mm, or about 4 mm to about 6 mm from the inner surface of the cranial bone (e.g., 0.1, 0.2±0.1, 0.4±0.1, 0.6±0.1, 0.8±0.1, 1±0.5, 2±0.5, 3±0.5, 4±0.5, 5±0.5, 6±0.5, 7±0.5, or 8±0.5 mm from the inner surface of the cranial bone). The inner surface of the cranial bone defines, in part, a space containing brain tissue.

In some embodiments, the at least one electrode is positioned within the cranial bone such that at least a portion of the first side extends above the outer surface of the cranial bone. In other embodiments, the at least one electrode is positioned within the cranial bone such that none of the first side extends above the outer surface of the cranial bone.

In some embodiments, the component further includes insulation, wherein the insulation is positioned around at least a portion of the first side. In certain embodiments, the component further includes threads adapted for securing the at least one electrode in the cranial bone. In particular embodiments, the threads are formed from an insulating material.

In specific embodiments, the component further includes one or more electrically conductive materials (e.g., a conductive cement and/or paste) in contact with the second side, in which the electrically conductive materials are positioned between the second side and the inner surface of the cranial bone. In various embodiments, the one or more electrically conductive materials is a conductive cement and/or paste.

In various embodiments, the second side is in direct contact with the cranial bone. In certain embodiments, the at least one electrode is laterally isolated, e.g., with a space between the active component and the cranial bone or an insulating element positioned around the active component.

In some embodiments the at least one electrode can include a conductive mesh. In various embodiments, the at least one electrode includes the shape of a lens, needle, disc, cone, or hemisphere.

In various embodiments, the electrical stimulation is delivered as direct current, cathodal direct current, anodal direct current, alternating current, or any combination thereof. In certain embodiments, the electrical stimulation is delivered as sustained current, as pulsed current, in a specific pulse pattern, as sustained voltage, as pulsed voltage, or any combination thereof.

In some embodiments, the electric stimulation is delivered at a frequency of about 0.1 Hz to about 2500 Hz (e.g., at a frequency of about 10 Hz to about 250 Hz). In various embodiments, the electric stimulation is delivered at a pulse width of about 10 μsec to about 10 sec (e.g., at a pulse width of about 50 μsec to about 250 msec). In some embodiments, the electric stimulation is delivered at a voltage of about 1 V to about 40 V (e.g., at a voltage of about 2 V to about 10 V). In various embodiments, the electric stimulation is delivered at a current of about 100 μA to about 20 mA (e.g., about 100 μA to about 1,500 μA).

In some embodiments, the electrostimulation device is configured to deliver electrical stimulation to one or more specific brain tissue volumes. In particular embodiments, the at least one electrode has at least one outer conductive element and a central conductive element. In certain embodiments, the at least one outer conductive element forms a symmetric configuration about the central conductive element. In alternative embodiments, the at least one outer conductive element forms a concentric configuration about the central conductive element. In various embodiments, the conductive elements are arranged in a geometric configuration including a ring, a square, a rectangle, an ellipse, or a polygon including any number of edges. In specific embodiments, the electrostimulation device is adapted to detect electrical activity within the brain tissue.

In various embodiments, the electrostimulation device includes a power supply (e.g., an external power supply, such as a battery connected to the electrodes by wires or wirelessly). In further embodiments, the electrostimulation device includes a control module, in which the control module is operatively coupled to the power supply and the electrode.

In particular embodiments, the electrostimulation device further includes an array of electrodes, wherein each electrode in the array conforms with the description above.

In various embodiments, the method can be used to detect, prevent, and/or treat a neurological disorder. For instance, the neurological disorder may include epilepsy, Parkinson's disease, Alzheimer's disease, migraine, stroke symptoms, pain, tinnitus, depression, insomnia, anxiety, or any combination thereof. In further embodiments, the method may also be used to treat, inhibit, and/or arrest the growth of a tumor (e.g., an intracranial neoplasm (e.g., a glioblastoma)).

In preferred embodiments, the subject is a mammal (e.g., a human).

A fourth aspect of the invention features an electrostimulation device including a power source electrically coupled to a component including at least one electrode within cranial bone of a subject, in which the at least one electrode includes a first side coupled to the power source and proximate to an outer surface of the cranial bone, and a second side proximate to an inner surface of the cranial bone, in which the second side is configured to be positioned about 0.1 mm to about 8 mm, about 2 mm to about 8 mm, about 4 mm to about 8 mm, about 0.1 mm to about 2 mm, about 2 mm to about 6 mm, about 2 mm to about 4 mm, or about 4 mm to about 6 mm from the inner surface of the cranial bone (e.g., 0.1, 0.2±0.1, 0.4±0.1, 0.6±0.1, 0.8±0.1, 1±0.5, 2±0.5, 3±0.5, 4±0.5, 5±0.5, 6±0.5, 7±0.5, or 8±0.5 mm from the inner surface of the cranial bone). The inner surface of the cranial bone defines, in part, a space containing brain tissue. The electrostimulation device is configured to deliver electrical stimulation to the brain tissue in the space.

In some embodiments, the component further includes threads adapted for securing the at least one electrode in the cranial bone. In certain embodiments, the threads are formed from an insulating material.

In particular embodiments, the component further includes one or more electrically conductive materials e.g., a conductive cement and/or paste) in contact with the second side, e.g., in which the electrically conductive materials are positioned between the second side and the inner surface of the cranial bone. In various embodiments, the one or more electrically conductive materials is a conductive cement and/or paste.

In certain embodiments, an electrostimulation device may be configured for the method of any of the above embodiments of the first aspect of the invention.

Definitions

As used herein, "about" refers to an amount ±10% of the recited value.

As used herein, "a" and "an" mean "at least one" or "one or more" unless otherwise indicated. In addition, the singular forms "a", "an", and "the" include plural referents unless the context clearly dictates otherwise.

The term "cranial bone," as used herein, refers to any of the bones surrounding the brain. The skull is comprised of cranial and facial bones. As used herein, the term "above" the cranial bone refers to the space between the cranial bone and the scalp and includes the scalp. As used herein, the term "below" the cranial bone refers to the area within the cranial bone, which includes cerebrospinal fluid and brain tissue.

The term "electrode", as used herein, refers to an electric conductor through which an electric current enters or leaves an electrolytic cell or other medium. It further refers to the geometric configuration of discrete type electrical conductive elements capable of causing an electromagnetic field when a current and voltage is applied. The electrode can be of any shape and symmetrically or unsymmetrically configured. In particular, the electrode is a cylindrical or slightly conical shape (e.g., with a cylinder length to diameter (l/d) ratio of about 0.3 to about 5, such as an l/d ratio is about 0.3 to about 0.5) including a first side and a second side, such as the at least one electrode is configured to be positioned in cranial bone with the first side proximate to an outer surface of the cranial bone and the second side proximate to an inner surface of the cranial bone (e.g., about 0.1 mm to about 8 mm from the inner surface of the cranial bone). The electrode can include one or more materials that promote osteoblast adhesion (e.g., high purity titanium, a titanium alloy, aluminum oxide, bioactive glass, hydroxyapatite, a ceramic-coated metal, calcium phosphate, cobalt-chromium, zirconium oxide, barium aluminate, barium titanate, iron oxide, or zinc oxide). The electrode is adapted for placement within the cranial bone, such that the first side is proximate to an outer surface of the cranial bone and the second side is proximate to an inner surface of said cranial bone, to deliver electrical stimulation and/or monitor electrical activity in the brain tissue of the patient (e.g., a human). In particular, the electrode may have a surface roughness (Sa) of about 0.5 μm to about 3.0 μm on the second side of the electrode. Arrays of electrodes (e.g., cylindrical or slightly conical electrodes) can be constructed from multiple discrete electrodes.

The term "electrostimulation device", as used herein, refers to a device including a power source electrically coupled to a component including at least one electrode (e.g., an electrode having a cylindrical or slightly conical shape). The electrostimulation device includes at least one electrode is adapted for placement within the cranial bone to deliver electrical stimulation and/or monitor electrical activity in the brain tissue of the patient (e.g., a human). The electrostimulation device can be adapted for delivery of a stimulating pulse or defined pulse pattern to the targeted tissue using a stimulation algorithm. The device may further include, e.g., a control module operatively coupled to the power supply and a stimulation sub-system and/or a switching sub-system when the device includes electrode arrays. In addition to the one or more electrodes, the component of the electrostimulation may include threads (e.g., multiple-start or buttress threads) for securing the electrode in the patient's cranial bone, a counter electrode with insulating materials between the center electrode and counter electrode, electrically conductive materials (e.g., conductive cement and/or paste), insulating materials (e.g., silicone, plastic, rubber, ceramic, or glass), and/or an external abutment on the first side of the electrode (e.g., proximate to an outer surface of the cranial bone), such as an external abutment connected to a compartment of the electrode (e.g., a compartment including the power source and/or additional components). The at least one electrode of the electrostimulation device may be completely submerged within the cranial bone, such as by placing the electrode into a cavity within the bone (e.g., including electrically conductive materials, such as bone cement or paste), or extend above the outer surface of the cranial bone. The component of the electrostimulation device may also be located, e.g., in part, within the cranial bone and/or outside of the cranial bone, such as between the cranial bone and scalp. The power supply of the electrostimulation device may be positioned, e.g., in a compartment with the electrode within the cranial bone, between the cranial bone and the scalp of the patient, or outside of the scalp of the patient.

The term "neurological disorder" or "neurological disorders", as used herein, refers to any disorder, disease, syndrome and/or symptom due to or resulting from neurologic, psychiatric, psychological, and/or cerebrovascular symptomology or origin, and includes diseases, disorders, or conditions of the brain and nervous system or psychiatric disorders or conditions. Neurological disorders include, without limitation, epilepsy, Parkinson's disease, Alzheimer's disease, migraine, stroke symptoms, pain, tinnitus, depression, insomnia, anxiety, or any combination thereof.

The term "power source," as used herein, refers to a component that supplies electrical energy to an electrostimulation device including an electrode. For example, a power source may include a battery from which the electrostimulation device obtains energy, such as a conventional battery or a wireless battery (e.g., a wireless rechargeable battery). A power source may also include, e.g., an electrical energy transmission system, a fuel cell, a generator, or an alternator. The power source of the electrostimulation device may be positioned within the electrode of the device that is imbedded in a patient's cranial bone, within a compartment adjacent to the electrode that is also imbedded in the cranial bone, or external to the patient. An external power source may be positioned on the body of the patient (e.g. in the chest of the patient) and/or may contain an antenna to send electrical impulses from the external power source directly to the electrodes imbedded in the cranial bone.

The term "stimulation", as used herein, refers to the use of an electrical signal or signals applied to neural tissue to stimulate or inhibit the formation of action potentials (e.g., brain tissue) via the scalp, skull, or near the tissue, in close proximity to the tissue, or to the skin surface, such as on the face, spine, or neck. Stimulation may also refer to the use of an electromagnetic signal or signals applied to neural tissue (e.g., brain tissue).

The terms "treatment," "medical treatment," to "treat," and "therapy", as used herein, refers to administering or exposing a subject to stimulation of the brain or nervous system, such as by one or more stimulating electrodes, or to some other form of medical intervention used to treat or prevent a disease, disorder, or condition (e.g., electromagnetic stimulation, a drug, surgery, or combinations thereof). For instance, the disease to be treated is epilepsy or symptoms of epilepsy (e.g., epileptic seizures). Diseases treated with the present invention may further include chronic epilepsy and other neurological diseases or psychiatric disorders or conditions.

The terms "patient" and "subject," as used interchangeably herein, refer to any mammal (e.g., a non-human mammal or a human). A patient to be treated or tested for responsiveness to a treatment according to the methods described herein may be one who has been diagnosed with epilepsy or a disease, disorder, or condition of the brain and nervous system.

The recitation herein of numerical ranges by endpoints is intended to include all numbers subsumed within that range (e.g., a recitation of 1 to 5 includes 1, 1.5, 2, 2.75, 3, 3.80, 4, and 5).

Other features and advantages of the invention will be apparent from the following detailed description, the drawings, and the claims.

DETAILED DESCRIPTION OF THE INVENTION

Figure 1:
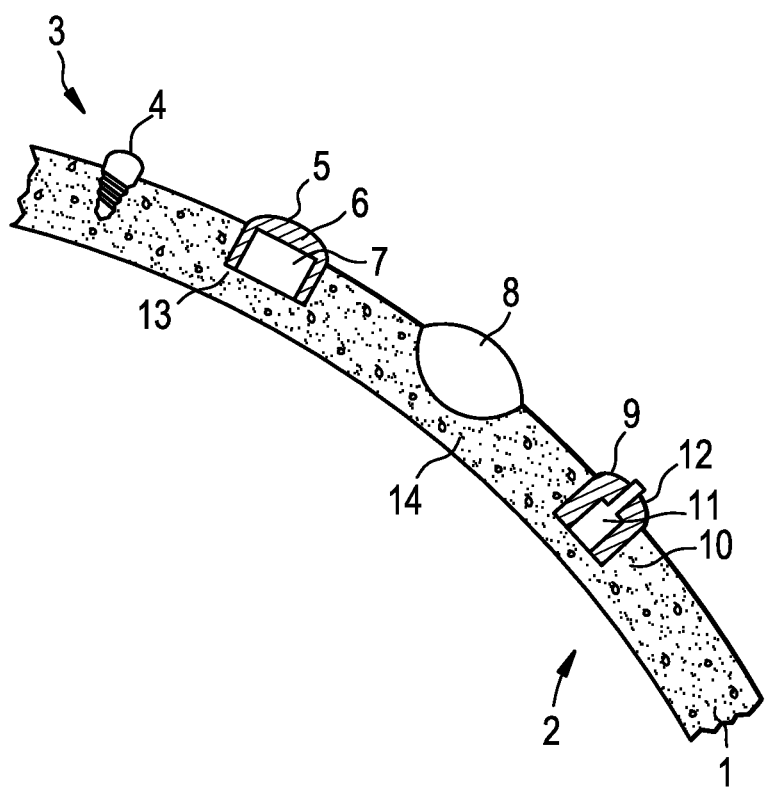
FIG. 1 is a schematic showing a coronal section of one hemisphere of the human head and exemplary electrode configurations according to the present invention (skin, brain tissue, spinal fluid, and other anatomical structures, except for the skull, are not shown). Dimensions provided in the FIG., if any, are for illustrative purpose only; the dimensions of the actual device(s) may be different. Although the electrodes are shown in a two-dimensional representation, in reality, the singular electrodes and electrode arrangements are three-dimensional within the skull (i.e., the cranial bone). Wiring to and from the electrodes may not be shown on the drawings for simplicity purposes.

There is a lack of minimally invasive, implantable electrostimulation devices with reduced space and power requirements relative to currently available extracranial devices. We have discovered that electrodes of an electrostimulation device may be imbedded in the skull (i.e., the cranial bone) of a patient (e.g., a human) to provide less invasive methods than presently available intracranial systems and less power-consuming options than presently available extracranial systems. The devices and methods of the present invention improve upon prior techniques in reducing the effective electrical resistance by decreasing the current distance through bone, by avoiding impedance problems by flush mounting electrodes to bone, and by avoiding current leakage through the scalp. Furthermore, imbedding electrodes into the cranial bone reduces corrosion associated with the exposure of metallic electrodes to liquid electrolytes.

In particular, the devices of the invention feature cylindrical or slightly conical shape electrodes composed of materials that promote osteoblast adhesion. Integration of the electrodes into the surrounding cranial bone is critical for successful bone regeneration and healing. The disclosed cranial electrodes are designed to optimize the interface between the electrode and cranial bone of the patient (e.g., a human), while avoiding or minimizing the risk of rejection by the patient as a result of, e.g., an immune response. The surface morphology of the electrodes is designed for implantation in the cranial bone. Electrodes can be characterized as having a cylinder length to diameter (l/d) ratio of about 0.3 to about 5 (e.g., a l/d ratio of about 0.3, about 0.5, about 0.7, about 0.9, about 1.1, about 1.3, about 1.5, about 1.7, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8, or about 5) and/or a surface roughness (Sa) of about 0.5 µm to about 3.0 µm (e.g., about 0.5 µm, about 1.0 µm, about 1.5 µm, about 2.0 µm, about 2.5 µm, or about 3.0 µm on the second side of at least one electrode. In particular, the l/d ratio is about 0.3 to about 0.5. Additionally, the electrostimulation devices are designed to minimize power and space requirements of the device, thereby reducing the invasiveness of the implantation and increasing the effectiveness of treatment. For example, the power source of the device (e.g., rechargeable batteries) and/or additional device components (e.g., a counter electrode) may be included in a compartment of the electrode, which is adapted to be completely submerged in the cranial bone.

The methods disclosed herein pertain to the use of less invasive electrostimulation devices than extracranial devices, which feature intracranial electrodes, to treat or prevent neurological events, such as epileptic seizures, than direct stimulation of brain tissue. Thus, an objective of the present invention is to provide devices and methods for electrical stimulation of the brain and nervous system, e.g., from a location within the cranial bone, that may be for acute or chronic treatment or suppression of neurological disorders, which includes diseases, disorders, or conditions of the brain and nervous system or psychiatric disorders or conditions.

Methods and devices of the present invention may be used for responsive stimulation to adverse neurological events (e.g., seizures (e.g., epileptic seizures)). The present invention also pertains to methods for preventing and/or treating neurological disorders utilizing such devices. These methods may further include detecting or sensing of neurological disorders prior to or during preventing or treating. For instance, stimulation from electrodes within the cranial bone may be used to alter the onset of abnormal electrical activity within the patient's brain. Furthermore, the present invention provides methods for the treatment, inhibition, or arrestment of the growth of a tumor (e.g., an intracranial neoplasm (e.g., a glioblastoma)).

Device Components

Various possible and optimal configurations of the stimulating electrodes are provided herein. FIG. 1 illustrates a coronal section of one hemisphere of the human head. Shown is the cross section of the cranial bone 1. The space on the left hand side of the cranial bone 1 is defined as "below" the cranial bone 1 and includes the brain 2 and physiological fluid. The space on the right hand side of the cranial bone 1 is defined as "above" the cranial bone 1 and is the space between the cranial bone and scalp and includes the scalp. As shown in FIG. 1, electrodes of the present invention may be adapted to different configurations within cranial bone 1.

In one example, the electrode within cranial bone 1 is a simple screw 4, which may include metal or conductive ceramic. In a second example, a hole 13 is drilled into cranial bone 1, and the electrode 5 is placed into hole 13. In this configuration, the electrode 5 includes isolation 6 from the cranial bone around the conductive, active component 7, e.g., a space between the active component and the cranial bone or an insulating element positioned around the active component. On the side of the cranial bone 1 in closest proximity to the brain tissue 2, the electrical current from electrode 5 may penetrate the bone. For instance, hole 13 may extend through a majority of the thickness of cranial bone 1, with a second side proximate to the inner surface of the cranial bone and a first side coupled to a power source.

In a third example, the electrode 8 is lens-shaped and located in a carved out location 14 of the cranial bone 1. The method for carving out the bone material may involve drilling, chiseling, grinding, milling, and/or polishing. In a fourth example, the electrode 9 within the cranial bone 1 is a screw 12 with a conductive inner core 11 and an isolated outer thread 10.

Figure 2:
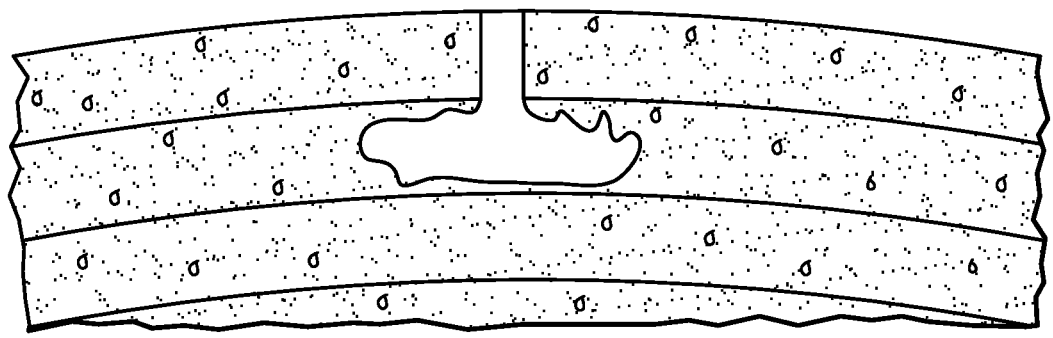
FIG. 2 is a schematic showing an electrode formed by filling a cavity in the cranial bone with conductive material.
Figure 3:
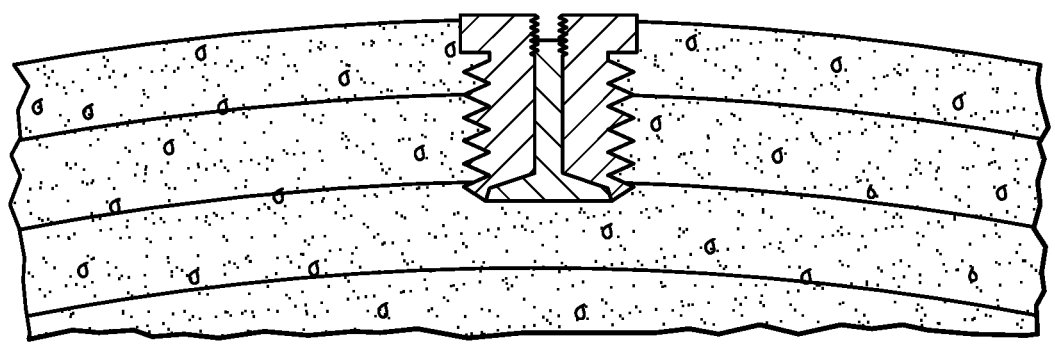
FIG. 3 is a schematic showing an electrode extending from the surface of the cranial bone into the cranial bone.
Figure 4:
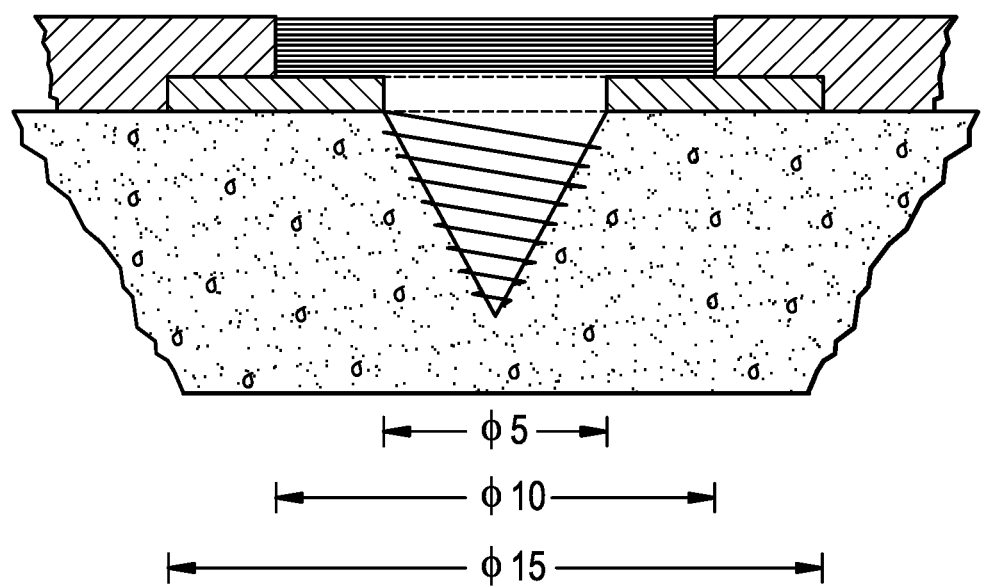
FIG. 4 is a schematic showing an electrode extending from the surface of the cranial bone into the cranial bone.
Figure 5:
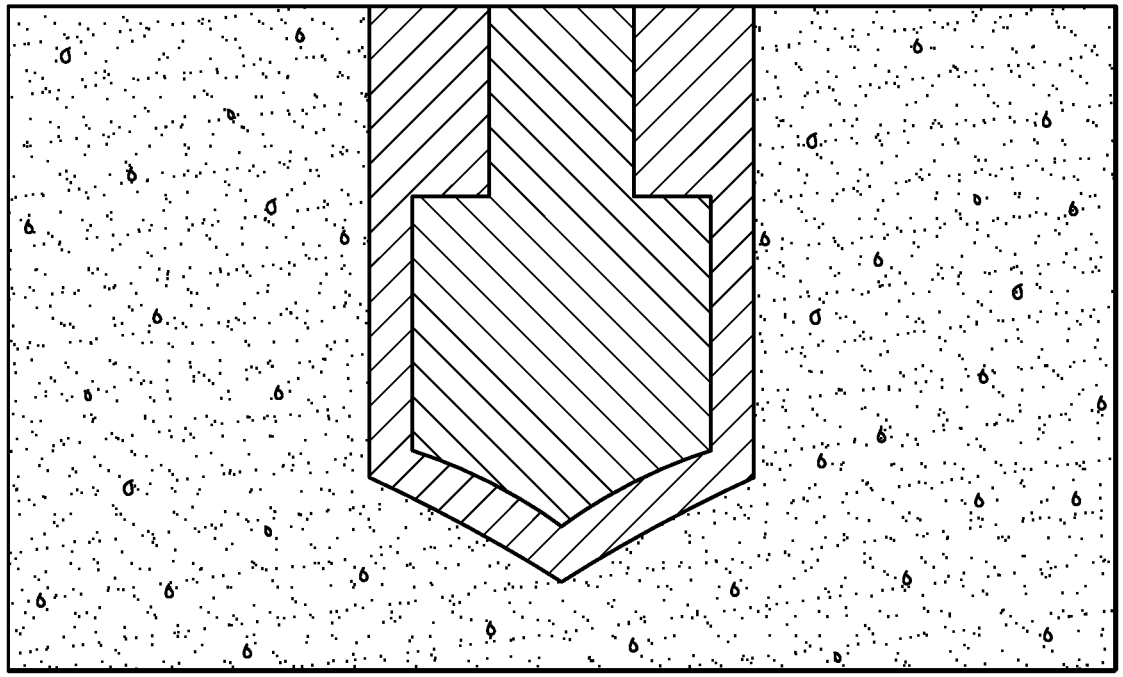
FIG. 5 is a schematic showing a cone-shaped electrode embedded in the cranial bone.
Figure 6:
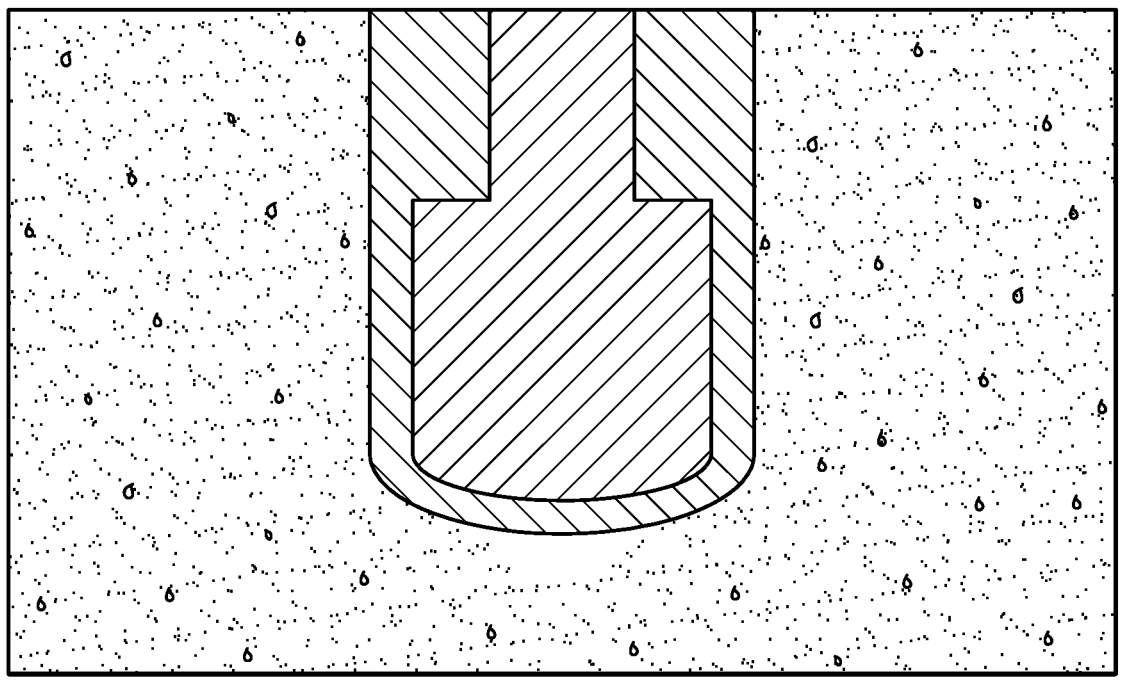
FIG. 6 is a schematic showing a hemispherical-shaped electrode embedded in the cranial bone.
Figure 7:
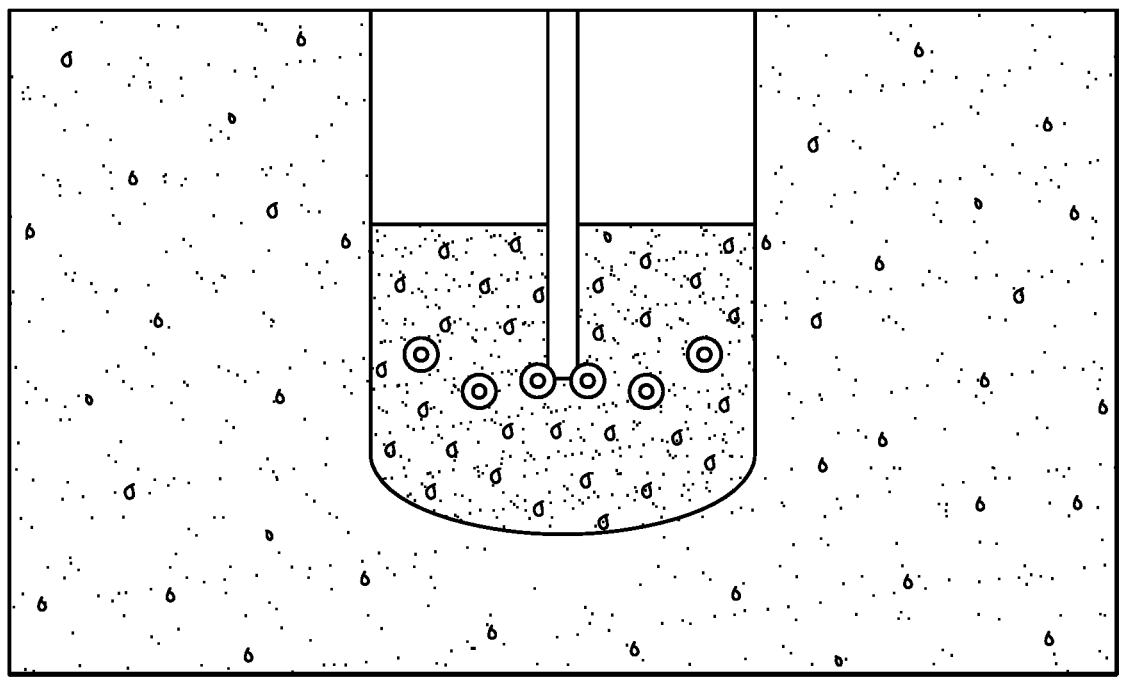
FIG. 7 is a schematic showing a conductive mesh electrode embedded in the cranial bone.

As shown in FIGS. 2-4, electrodes of the present invention may be embedded into the cranium, extending from the surface into the cranial bone. For instance, a cranial electrode may be formed by replacing the excised cranial bone with electrically conductive materials, e.g., conductive bone cement (a mixture of bone cement and conductive particles) (see FIG. 2).

Figure 8:
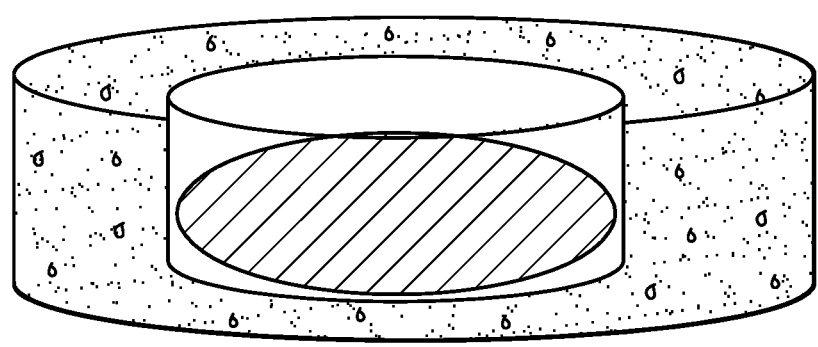
FIG. 8 is a schematic showing a disc electrode with a tangentially fixed lead embedded in the cranial bone.

As shown in FIGS. 5-8, electrodes embedded into the cranium may also be completely submerged in the cranial bone. Complete submersion of the electrode within the cranial bone may be achieved by placing the electrode into a cavity within the bone. Volume remaining in the bone cavity after placement of the electrode may be filled with a non-conductive or conductive material (e.g., bone cement). Electrodes submerged into the cranial bone may include cone-shaped electrodes (FIG. 5), hemispherical-shaped electrodes (FIG. 6), conductive mesh electrodes (FIG. 7), and/or disc electrodes with a tangentially fixed lead (FIG. 8).

Figure 9C:
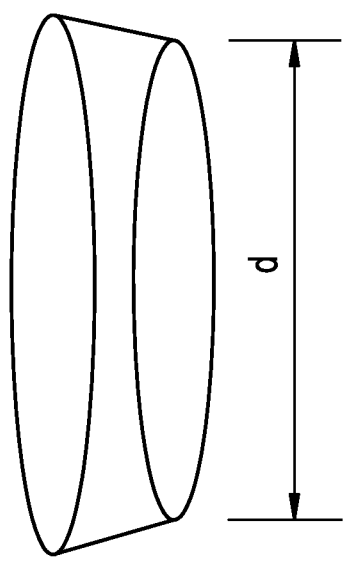
FIGS. 9A-9C are schematics showing the length to diameter (l/d) ratio and shape of an electrode of the invention. An exemplary l/d ratio is about 0.3 to about 5 (FIG. 9A). The exemplary electrodes are cylindrical (FIG. 9B) or slightly conical (FIG. 9C).
Figure 9B:
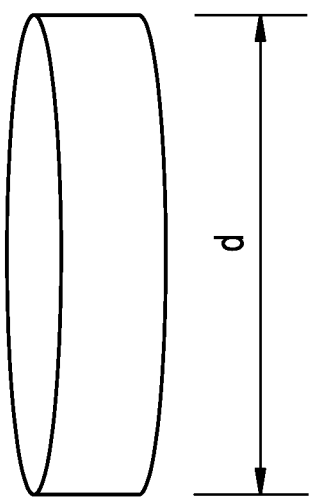
Figure 9A:
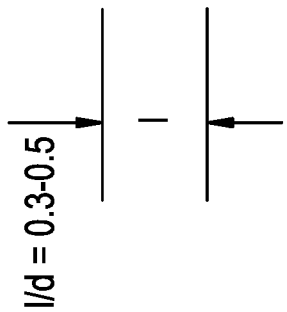

As shown in FIGS. 9A-9C, exemplary electrodes of the invention are cylindrical or slightly conical shape with a cylinder length to diameter (l/d) ratio optimized for implantation in cranial bone of a patient (e.g., a human). These electrodes can be employed for both the electrical stimulation of brain tissue and/or detection of brain activities. An exemplary l/d ratio of an electrode is about 0.3 to about 5.0 (FIG. 9A). For example, the l/d ratio of the electrode can range from about 0.5 to about 4.5, about 1.0 to about 4.0, about 3.0 to about 5.0, about 1.0 to about 3.0, about 0.7 to about 3.0, about 0.3 to about 5.0, about 1.5 to about 5.0, about 2.0 to about 4.5, about 3.5 to about 5.0, about 2.5 to about 4.0, about 0.5 to about 3.0, or about 1.5 to about 2.5. In particular, the l/d ratio of the electrode can be, e.g., about 0.3, about 0.5, about 0.7, about 0.9, about 1.1, about 1.3, about 1.5, about 1.7, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8, or about 5.0. In particular, the l/d ratio is about 0.3 to about 0.5.

The length of the electrode and additional, optional components (e.g., a counter electrode) of the electrostimulation device depends on the thickness of the cranium at the site of implantation. For example, the length of the device component including the electrode can range from about 2 mm to about 8 mm, such as about 2 mm to about 6 mm, about 4 mm to about 8 mm, about 5 mm to about 7 mm, about 2 mm to about 5 mm, about 3 mm to about 8 mm, about 2 mm to about 7 mm, about 4 mm to about 6 mm, about 2 mm to about 3 mm, about 4 mm to about 7 mm, about 6 mm to about 8 mm, or about 3 mm to about 5 mm. In particular, the length of the device component including the electrode can be, e.g., about 2 mm, about 2.2 mm, about 2.4 mm, about 2.6 mm, about 2.8 mm, about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.5 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, or about 8.0 mm.

For example, electrodes of the electrostimulation devices can be cylindrical (FIG. 9B) or slightly conical (FIG. 9C), and similar in shape to, e.g., coin cells. The diameter of the electrode can be, e.g., about 4 mm to about 12 mm, such as about 4 mm to about 10 mm, about 6 mm to about 12 mm, about 8 mm to about 11 mm, about 4 mm to about 9 mm, about 6 mm to about 8 mm, about 10 mm to about 12 mm, about 4 mm to about 5 mm, about 4 mm to about 12 mm, about 5 mm to about 8 mm, about 6 mm to about 9 mm, or about 9 mm to about 12 mm.

Figure 10:
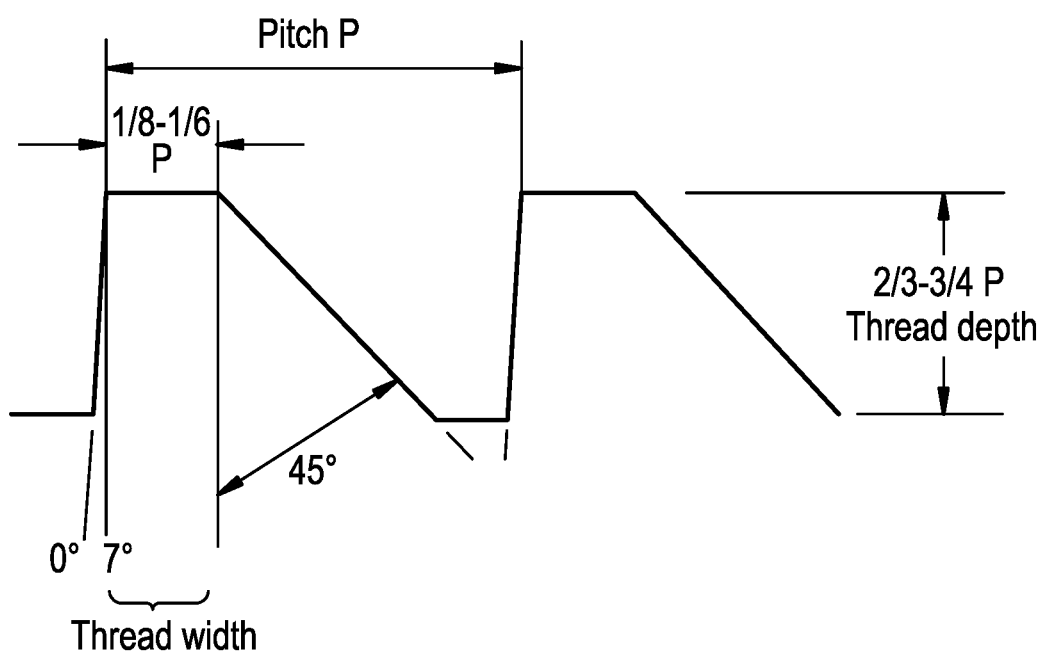
FIG. 10 is a schematic showing the dimensions of a buttress thread including the thread width, pitch, and thread depth. The load-bearing thread face of the thread is perpendicular to the screw axis or at a slight slant at less than 7°. The other face is slanted at 45°. The pitch and shape of the thread support the cranial bone-to-implanted device contact and the biomechanical load distribution. The thread width can range from about ⅛ to about ⅙ of the thread pitch, while the thread depth can range from about ⅔ to about ¾ of the thread pitch.

As shown in FIG. 10, an exemplary thread for use in the electrostimulation devices can be a buttress thread. Various shapes and embodiments of threads may be used in the electrostimulation devices to attach the device component including the electrode to the cranial bone. Preferably, the electrostimulation device includes threads with bone-condensing properties, such as buttress threads. In particular, the compressive force of buttress threads dissipates potential stresses at the interface between the device component including the at least one electrode and the cranial bone. The load-bearing thread face of the thread is perpendicular to the screw axis or at a slight slant at less than 7° (e.g., about 1°, about 2°, about 3°, about 4°, about 5°, about 6°, or about 7°), while the other face of the buttress thread is slanted at about 45°. The thread width can range from about ⅛ to about ⅙ of the thread pitch, while the thread depth can range from about ⅔ to about ¾ of the thread pitch.

Threads for use in the electrostimulation devices of the invention may be composed of one or more insulating materials, such as silicone (e.g., hard silicone with a high shore), plastic, rubber, ceramic, or glass, and/or one or more electrically conductive materials, such as conductive cement or paste. The threads can be, e.g., self-cutting, single-start, or multiple-start threads. In particular, the threads are self-cutting for ease in handling of the threads during, e.g., implantation in the cranial bone. Threads may also be single-lead or multiple-lead threads. The lead of a thread indicates the distance that an implant moves after one turn, which affects the implantation of the electrodes in the cranial bone due to the surface area and insertion speed of the thread. Multiple-lead threads, in which two or more threads run parallel to one another, allow for faster insertion of the electrode and associated compartments in the cranial bone because the lead increases as a function of the number of threads times the pitch.

Figure 11:
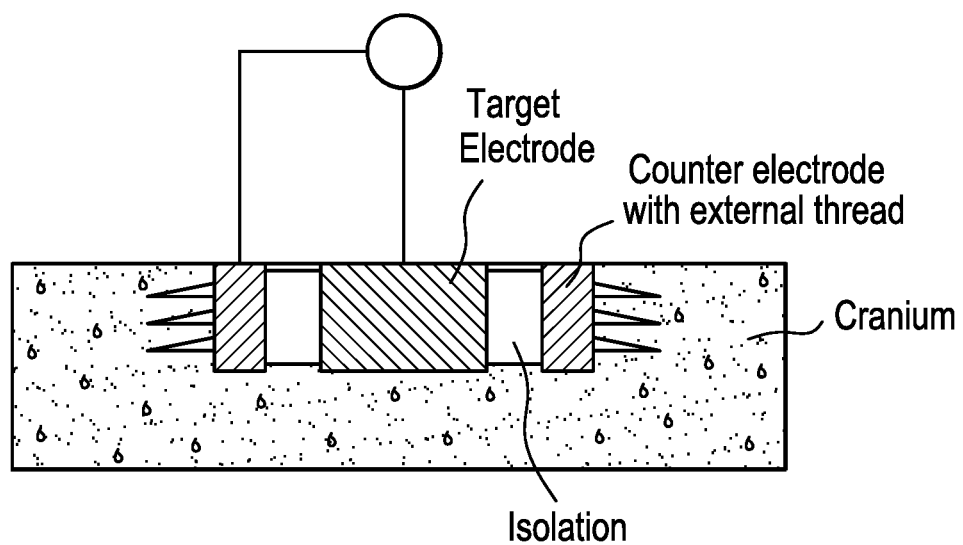
FIG. 11 is a schematic showing an electrostimulation device including a cylindrical electrode and counter electrode surrounding the central, cylindrical electrode embedded in cranial bone and separated by one or more insulating materials. The counter electrode includes external threads adapted for securing the electrode in cranial bone.

As shown in FIG. 11, the electrostimulation device can include a cylindrical electrode and counter electrode surrounding the central, cylindrical electrode embedded in cranial bone of a patient (e.g., a human). The central electrode and counter electrode are separated by one or more insulating materials, such as silicone, plastic (e.g., a biocompatible plastic, such as polyether ether ketone (PEEK)), rubber, ceramic, or glass, with the central electrode fixed (e.g., screwed or glued) within the cylindrical hollow body. The counter electrode includes external threads adapted for securing the electrode in cranial bone. The central target electrode and counter electrode are connected by electrical leads. The excised cranial bone may be replaced with electrically conductive materials, e.g., conductive bone cement (a mixture of bone cement and conductive particles). The first side of the electrode is proximate to an outer surface of the cranial bone, and the second side of the electrode is proximate to an inner surface of the cranial bone that includes, in part, a space containing brain tissue.

Figure 12:
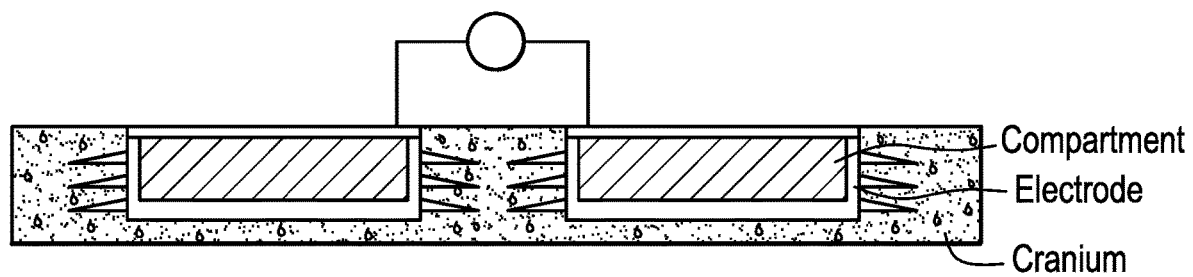
FIG. 12 is a schematic showing two cylindrical electrodes embedded within the cranial bone and connected externally to the cranial bone, such as with electrical leads.

As shown in FIG. 12, the electrostimulation device can include two cylindrical electrodes embedded within cranial bone of a patient (e.g., a human) and connected externally to the cranial bone, such as with electrical leads. The electrostimulation device can also include, e.g., 3, 4, 5, 6, 7, 8, 9, 10, 11, 12, 13, 14, 15, 16, 17, 18, 19, or 20 cylindrical or slightly conical electrodes, such as electrodes arranged in an array and configured for implantation in the cranial bone. The electrodes may be employed as unipolar electrodes with other conductive electrostimulation device components serving as a counter electrode.

Each electrode can include an internal compartment within the device component configured for implantation within cranial bone or adjacent to the electrode containing additional components, such as a power source (e.g., a wireless power source), configured to be embedded in the cranial bone. Additionally, the power source can be implanted and reside within the cranial bone in a compartment of the device component and adjacent to the one or more electrodes or the power source can be located external to the body of the patient, such as positioned on the body of the patient (e.g., in the chest of a patient). For example, an external power source located outside the patient's body may contain an antenna, such that electrical impulses may be sent from the external power source directly to the electrode (s) embedded in cranial bone, which can, e.g., have the benefits of reducing the size of the implanted device component including the electrode and prevent the need for surgeries to replace the battery of the electrostimulation device. The electrostimulation device can also contain a control module operatively coupled to the power supply and one or more stimulating electrodes. For example, the power supply can be a conventional battery or a wireless, such as a rechargeable, wireless battery. For a power source residing outside of the cranial bone, the external power source can be coupled via wires, or wirelessly via an inductively coupled coil.

Figure 13:
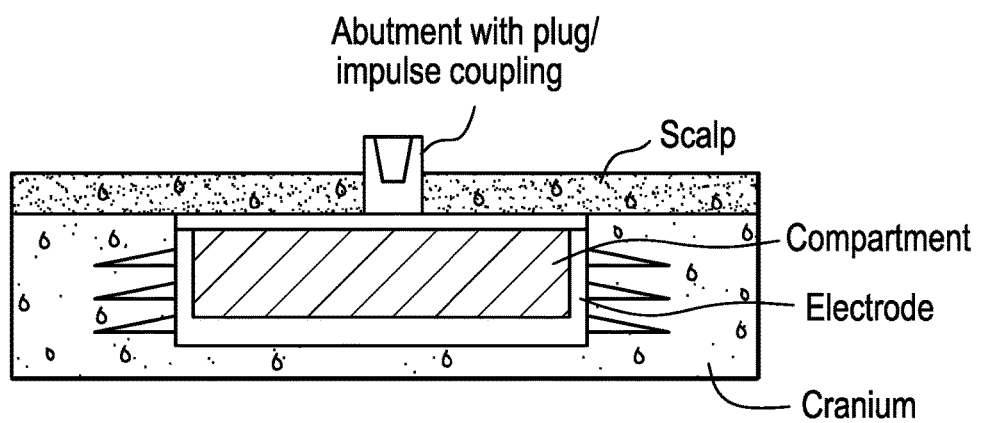
FIG. 13 is a schematic showing an electrostimulation device including an abutment on the first side of the electrode proximate to an outer surface of the cranial bone, which provides external access to the electrode within cranial bone.

As shown in FIG. 13, the electrostimulation device can further include an abutment on the first side of the electrode proximate to an outer surface of the cranial bone. The abutment of the device component can be located outside the scalp of the patient (e.g. a human), thereby providing external access to the electrode within the cranial bone. If the device component including the cylindrical electrode has a compartment, then the size of the electrostimulation device can be reduced by including the power source (e.g., a battery or a wireless power source, such as a wireless, rechargeable battery) within the compartment, and the abutment connected to the compartment will facilitate access to the power source (e.g., a battery or a wireless power source, such as a wireless, rechargeable battery) for re-charging. Because batteries are often the largest component of an electrostimulation device, this configuration is advantageous in reducing the space requirements of the device. Moreover, all components of an electrostimulation device, which may include, but are not limited to, the power source (e.g., wireless power source, such as a wireless battery), counter electrode, control module operatively coupled to the power supply, stimulation sub-system, analysis sub-system, switching sub-system, and/or plurality of electrodes, can be integrated into the device component including the cylindrical electrodes for implantation in cranial bone of a patient (e.g., a human). In particular, a wireless power source could be included in the electrostimulation device for implantation in the cranial bone and controlled external to the patient with a control module, thereby reducing the space requirements of the implanted device. Wireless power transfer to an implanted portion of an electrostimulation device including a wireless power source may be achieved via, e.g., inductive coupling. Wireless power transfer has the advantage of allowing for a reduction in battery size relative to traditional electrostimulation devices, such that the implanted portion of the electrostimulation device is minimally invasive and compact for implantation in the cranial bone. Additionally, such electrostimulation devices of the present invention are advantageous in eliminating the need for invasive, repeated surgeries to replace the battery after implantation of the electrostimulation device. In particular, inductive coupling may provide benefits and reliable control of a wireless power source of the electrostimulation device relative to conventional methods of wireless power transfer, such as piezoelectric, thermoelectric, or ultrasound based methods. Notably, implantable electrodes of the present invention featuring a diameter of about 10 to 12 mm can include a relatively large (e.g., about 1 cm diameter or greater), coil-shaped antenna for wireless energy transfer in the cranial bone (e.g., an electrostimulation device positioned about 0.1 mm to about 8 mm from the inner surface of the cranial bone, such as about 0.5 mm to about 2 mm from the inner surface of the cranial bone). Additionally, wireless power transfer to an electrostimulation device of the invention may be achieved using, e.g., midfield power transfer, in which milliwatts (mW) of power may be transferred into the cranial bone using a patterned metal plate to induce spatially confined, adaptive energy transfer through the cranial bone. In particular, midfield power transfer may transfer power to, e.g., a coil-shaped antennae including within the portion of the electrostimulation device implanted in cranial bone.

Electrodes

Devices of the present invention may include one or more electrodes adapted for placement within the cranial bone of a patient (e.g., a human) to deliver electrical stimulation and/or monitor electrical activity in the patient's brain. The design of electrodes of the present invention is adjustable and may be realized in any form and configuration. For instance, electrodes may be needle-shaped or pencil-shaped, screwed, glued, or tuckered. Electrodes submerged into a cavity or cavities of the cranial bone may be disc-shaped, cone-shaped, or hemispherical electrodes. Disc-shaped electrodes may be laterally isolated and/or isolated from the cranial bone surface, in which the conductive side is in contact with the cranial bone. A conductive mesh or fiber bundle may also serve as an electrode. The conductive elements of the electrodes may be arranged in a geometric configuration of a ring, a square, a rectangle, an ellipse, or a polygon comprising any number of edges. As is described below, electrodes may be Laplacian or in a concentric configuration as well as symmetrical in design.

For example, electrodes can be cylindrical or slightly conical, similar in shape to, e.g., coin cells. Upon implantation in the cranial bone, the first side (e.g., proximate to an outer surface of the cranial bone) and the second side (e.g., proximate to an inner surface of the cranial bone) of the electrode anchors the electrostimulation device to the cranial bone of the patient. Additionally, the device component including the cylindrical or slightly conical electrode(s) can include additional components (e.g., a power source, a counter electrode, a control module operatively coupled to the power supply, a stimulation sub-system, an analysis sub-system, a switching sub-system, and/or a plurality of electrodes) within a compartment for implantation in cranial bone of a patient (e.g., a human).

When implanted in cranial bone, the second side of the electrode is positioned at least 0.5 mm from the inner surface of the cranial bone, such about 0.5 mm to about 8 mm, about 2 mm to about 8 mm, about 4 mm to about 8 mm, about 0.7 mm to about 2 mm, about 2 mm to about 6 mm, about 2 mm to about 4 mm, or about 4 mm to about 6 mm from the inner surface of the cranial bone (e.g., 0.1, 0.2±0.1, 0.4±0.1, 0.6±0.1, 0.8±0.1, 1±0.5, 2±0.5, 3±0.5, 4±0.5, 5±0.5, 6±0.5, 7±0.5, or 8±0.5 mm from the inner surface of the cranial bone). The inner surface of the cranial bone defines, in part, a space containing brain tissue. The second side of the electrode proximate to an inner surface of the cranial bone can be composed of materials optimized for a high charge injection capacity, such as high purity titanium, a titanium alloy, aluminum oxide, bioactive glass, hydroxyapatite, a ceramic-coated metal, calcium phosphate, cobalt-chromium, zirconium oxide, barium aluminate, barium titanate, iron oxide, and zinc oxide.

The two primary mechanisms that facilitate attachment of the device component including the electrode to the cranial bone of the patient include mechanical and biochemical attachment. The choice of material and the material's biocompatibility once implanted in the patient is key for biochemical attachment, while the surface roughness (Sa) of the electrode is critical for the mechanical attachment of the device component within the cranial bone. The surface characteristics at the interface between the component including the electrode and cranial bone promotes integration of the electrodes into the cranial bone of the patient (e.g., a human). For example, a high degree of bone contact and formation can be achieved by modifying the thickness and surface topography of the component (e.g., a titanium implant), which allows for anchoring of the implanted device component to the cranial bone.

Surface roughness (Sa) refers to the mean height of peaks and pits of the surface, such as the second side of the electrode proximate to an inner surface of the cranial bone. Various methods are known for engineering the Sa of the device compartment including the electrode for implantation in cranial bone. Exemplary methods for achieving a surface roughness (Sa) of the device component including the electrode include, but are not limited to, sandblasting, acid etching, anodic oxidation, laser modification, and/or plasma coating. Preferably, the processing sequence is sand-blasting followed by acid etching, which allows engineering of both surface roughness and thickness of the oxide layer for implantation in the cranial bone. The Sa after sandblasting is usually anisotropic, consisting of craters and ridges and occasionally particles embedded in the surface of the electrode. Acid etching (e.g., using HCl or HF) erodes the surface through selective removal of material and impurities, which are more sensitive to the etching, thereby producing micro pits with sizes ranging from about 0.5 µm to about 2 µm. The process of acid etching also removes residual particles, smoothens the profile of craters and ridges, and increases the thickness of oxide layers. Preferably, the second side of the electrode has a Sa of about 0.5 µm to about 3.0 µm, such as about 0.5 µm to about 2.0 µm, about 1.0 µm to about 2.5 µm, about 1.5 µm to about 2.5 µm, about 0.5 µm to about 1.5 µm, about 1.0 µm to about 2.0 µm, about 2.0 µm to about 3.0 µm, or about 1.5 µm to about 3.0 µm (e.g., about 0.5 µm, about 1.0 µm, about 1.5 µm, about 2.0 µm, about 2.5 µm, or about 3.0 µm). In particular, the Sa is about 1.0 µm to about 2.0 µm.

The conductive electrode of the present invention may be fabricated from a variety of metals (e.g., titanium, gold, platinum, or iridium), metal alloys, and nonmetals, such as conductive synthetic materials (e.g., conductive polymers), graphite, a mixture of graphite and silicone, or conductive ceramics (e.g., titanium nitride (TiN)) or any combination thereof that are biocompatible or have conductive biocompatible coatings. Such materials are typically used for stimulating electrodes in medical fields. In general, the isolating components of the electrode(s) may include high resistance or high impedance materials, such as plastics, silicones, rubbers, ceramics, or glasses.

The ability of the component including the electrode proximate to an inner surface of the cranial bone (e.g., the second side of the electrode) to adsorb organic molecules, such as proteins, is important for the biochemical attachment of the implanted device and depends on the material at the interface between implant and bone. Preferably, the electrode includes one or more materials that promote osteoblast adhesion, such as high purity titanium, a titanium alloy (e.g., Ti-6Al-4V, Ti-6Al-7Nb, or Ti-13Nb-13Zr), aluminum oxide (e.g., monocrystalline aluminum oxide or polycrystalline aluminum oxide), bioactive glass, hydroxyapatite, a ceramic-coated metal (e.g. titanium, gold, platinum, or iridium), calcium phosphate, cobalt-chromium, zirconium oxide, barium aluminate, barium titanate, iron oxide, and zinc oxide. In particular, high purity titanium is biocompatible and exhibits minimal allergic or rejection reactions upon implantation in bone.

Directing the current to specific brain regions can be achieved with specific configurations of electrodes, such as electrodes in a concentric configuration. This unique feature performs significantly better with concentric electrodes than with conventional electrodes because concentric ring electrodes enhance the localization process. A concentric or Laplacian electrode configuration may include at least one outer conductive element and one central conductive element, with the outer conductive element(s) surrounding the central conductive element. Concentric electrodes consist of a central disc and one or more concentric rings. The theoretical advantage of concentric ring electrodes is that the electric field and current density have a cylindrical symmetry because of the cylindrical symmetry of the electrode, which forces the current directly under the center of the ring to be perpendicular to the electrode. However, current densities of concentric ring electrodes are generally asymmetric due to inhomogeneous impedances of the tissue below the ring electrode.

The devices and methods disclosed herein may also include Pseudo-Laplacian electrodes. The term Pseudo-Laplacian electrodes is used for electrode arrays, which use discrete secondary electrodes positioned circularly of a specific diameter around a central targeting electrode. For instance, a ring structure of the targeting electrodes can be constructed by electrically connecting a number of discrete electrodes together. The advantage of pseudo-Laplacian electrode arrays with discrete electrodes over concentric ring electrodes is that the current flow through each of the electrodes can be individually controlled and adjusted. This configuration facilitates identical currents in each of the peripheral electrodes despite inhomogeneous impedances of the tissue below the electrodes and provides the option to control the current densities by varying the current applied to each of the discrete electrodes. Examples of concentric ring electrodes and other electrode arrangements capable of delivering stimulation to defined brain areas from a location between the scalp and the skull may be found in U.S. Pat. No. 8,190,248 and U.S. Patent Application No. US2011/0137381, the disclosures of which are incorporated herein by reference in their entireties.

Electrodes of the present invention may be used to deliver alternating current (AC) or direct current (DC) stimulation. In modes of DC stimulation, brain areas targeted for neuronal excitation are exposed to anodal stimulation, whereas brain areas targeted to inhibit neuronal activity are exposed to cathodal stimulation. The respective counter electrode may reside in a neutral area or in close proximity to brain tissues targeted for the opposite type of modulation (e.g., excitation or inhibition of neuronal activity). Thus, a bipolar mode of operation allows for the simultaneous inhibition and excitation of the activity associated with different brain tissue areas. During monopolar stimulation, the battery case may be used as the counter electrode.

Control Module and Subsystems

The electrostimulation device further includes a power supply (e.g., a battery unit) and may contain a control module operatively coupled to the power supply and one or more stimulating electrodes. For instance, an external power supply may be coupled via wires, or wirelessly via an inductively coupled coil. The control module may include a detection subsystem for detecting abnormal electrical activity within the brain and a responsive analysis subsystem for analyzing the abnormal electrical activity within the brain. A responsive stimulation subsystem is operatively controlled by the control module to deliver an electric responsive stimulation into the patient's brain in response to the responsive analysis subsystem.

Devices of the present invention may also include one or more sensing electrodes arranged in arrays or any other possible configuration and adapted for placement outside the patient's brain (e.g., within the cranial bone) to monitor electrical activity within the brain. The control module may include a subsystem operatively coupling the control module to the plurality of stimulating electrodes. The control module may select stimulating electrodes among the plurality of stimulating electrodes in order to switch selected electrodes between different patterns about the patient's brain without altering the placement of the plurality of stimulating electrodes.

Therapeutic Methods

The present invention pertains to methods for the treatment, detection, and/or prevention of neurological disorders or symptoms. The present invention further includes responsive and/or preventive stimulation methods featuring an electrostimulation device for the treatment of neurological disorders from a location within the cranial bone. Methods of the present invention may combine electric stimulation from electrodes located within the cranial bone with stimulation from electrodes or inductive coils located outside or inside the cranium. Methods of the present invention may also be useful for acute or chronic treatment or suppression of neurological disorders, which may be diseases, disorders, or conditions of the brain and nervous system or psychiatric disorders or conditions.

Methods of the present invention may also be used to treat, inhibit, and/or arrest the growth of a tumor (e.g., an intracranial neoplasm (e.g., a glioblastoma)). The present invention may be used to deliver electrical stimulation for the treatment of other neoplastic pathologies that may include, but are not limited to, medullar epithelomas, medulloblastomas, neuroblastomas, germinomas, embryocarcinomas, astrocytomas, astroblastomas, ependymomas, oligodendrogliomas, plexocarcinomas, neuroepithelomas, pineoblastomas, ependymoblastoma, neuroectodermic tumors, malignant meningiomas, chondrosarcomas, meningeal sarcomas, malignant melanomas, malignant schwannomas, or any combination thereof.

The present invention is, in part, directed to substrate modification, which involves altering the electrical properties of the brain by preventive chronic stimulation and/or responsive stimulation (e.g., in response to observed brain electrical activity). For instance, a method of the present invention may include the steps of positioning one or more sensing electrodes outside the patient's brain, detecting electrical activity within the brain consistent with a neurological event, and analyzing the neurological event to determine whether the neurological event is abnormal. The method may further include delivering a responsive stimulating current into the patient's brain through the one or more stimulating electrodes in response to detection of an abnormal neurological event.

Alternatively, a preventive stimulating current may be delivered into the patient's brain, independent of analyzing a neurological event, in order to alter the onset of the neurological event within the patient's brain. The method may further include the steps of positioning a plurality of stimulating electrodes outside the patient's brain and stimulating in a constant pattern, which may increase the threshold required for a neurological event to occur and may prevent future adverse neurological events. The plurality of stimulating electrodes may be of any type and configured in any form or shape.

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. An electrostimulation device comprising a power source electrically coupled to a component comprising at least one electrode comprising one or more materials that promote osteoblast adhesion, wherein said at least one electrode comprises a cylindrical or conical shape comprising a first side and a second side, wherein said at least one electrode is characterized by one or both of the following:
   (a) a cylinder length to diameter (l/d) ratio of about 0.3 to about 5.0; and/or
   (b) a surface roughness (Sa) of about 0.5 μm to about 3.0 μm on said second side of said at least one electrode, wherein the component further comprises a counter electrode.

2. The electrostimulation device of claim 1, wherein said one or more materials is selected from the group consisting of high purity titanium, a titanium alloy, aluminum oxide, bioactive glass, hydroxyapatite, a ceramic-coated metal, calcium phosphate, cobalt-chromium, zirconium oxide, barium aluminate, barium titanate, iron oxide, and zinc oxide.

3. The electrostimulation device of claim 1, wherein said component further comprises threads, wherein said threads are self-cutting, single-start, or multiple-start threads.

4. The electrostimulation device of claim 3, wherein said threads are bone-condensing threads.

5. The electrostimulation device of claim 4, wherein said threads are buttress threads.

6. The electrostimulation device of claim 3, wherein said threads are comprised of one or more insulating materials.

7. The electrostimulation device of claim 1, wherein said Sa is achieved by sandblasting, acid etching, anodic oxidation, laser modification, and/or plasma coating.

8. A method for stimulating brain tissue in a subject using an electrostimulation device comprising:
(i) positioning at least one electrode having a first side and a second side within cranial bone, wherein said first side of said at least one electrode is proximate to an outer surface of said cranial bone and said second side of said at least one electrode is proximate to an inner surface of said cranial bone, wherein said second side is configured to be positioned about 0.1 mm to about 8 mm from the inner surface of said cranial bone, and wherein the inner surface of said cranial bone defines, in part, a space containing brain tissue; and
(ii) delivering electrical stimulation to said brain tissue in said space,
wherein the electrostimulation device comprises a power source electrically coupled to a component comprising at least one electrode comprising one or more materials that promote osteoblast adhesion, and wherein said at least one electrode comprises a cylindrical or slightly conical shape comprising a first side and a second side, wherein said at least one electrode is characterized by one or both of the following:
(a) a cylinder length to diameter (l/d) ratio of about 0.3 to about 5.0; and/or
(b) a surface roughness (Sa) of about 0.5 μm to about 3.0 μm on said second side of said at least one electrode, wherein the component further comprises a counter electrode.

9. The method of claim 8, wherein said second side is positioned about 2 mm to about 8 mm from the inner surface of said cranial bone.

10. The method of claim 9, wherein said second side is positioned about 1 mm to about 4 mm from the inner surface of said cranial bone.

11. The method of claim 10, wherein said second side is positioned about 0.5 mm to about 2 mm from the inner surface of said cranial bone.

12. A method for stimulating brain tissue in a subject, comprising:
(i) providing an electrostimulation device comprising a power source electrically coupled to a component comprising at least one electrode;
(ii) positioning at least a portion of said at least one electrode within cranial bone, wherein said at least one electrode comprises a first side coupled to said power source and proximate to an outer surface of said cranial bone, and a second side proximate to an inner surface of said cranial bone, wherein said second side is configured to be positioned about 0.1 mm to about 8 mm from the inner surface of said cranial bone, and wherein the inner surface of said cranial bone defines, in part, a space containing brain tissue; and
(ii) delivering electrical stimulation to said brain tissue in said space.

13. The method of claim 12, wherein said second side is positioned about 2 mm to about 8 mm from the inner surface of said cranial bone.

14. The method of claim 13, wherein said second side is positioned about 4 mm to about 8 mm from the inner surface of said cranial bone.

15. The method of claim 12, wherein said second side is positioned about 0.1 mm to about 2 mm from the inner surface of said cranial bone.

16. The method of claim 12, wherein said at least one electrode is positioned within said cranial bone such that at least a portion of the first side extends above the outer surface of said cranial bone.

17. The method of claim 12, wherein said at least one electrode is positioned within said cranial bone such that none of the first side extends above the outer surface of said cranial bone.

18. The method of claim 12, wherein said component further comprises insulation, wherein said insulation is positioned around at least a portion of the first side.

19. The method of claim 12, wherein said component further comprises threads adapted for securing said at least one electrode in said cranial bone.

20. The method of claim 19, wherein said threads are formed from an insulating material.

21. The method of claim 12, wherein said component further comprises one or more electrically conductive materials in contact with said second side, or wherein said electrically conductive materials are positioned between said second side and the inner surface of said cranial bone.

22. The method of claim 21, wherein said one or more electrically conductive materials is a conductive ceramic and/or paste.

23. The method of claim 12, wherein said at least one electrode comprises a conductive mesh, a lens, a needle, a disc, a cone, or a hemisphere.

24. The method of claim 12, wherein said electric stimulation is delivered as direct current or as alternating current.

25. The method of claim 12, wherein said electric stimulation is delivered as sustained current, said electric stimulation is delivered as pulsed current, said electric stimulation is delivered in a specific pulse pattern, said electric stimulation is delivered as sustained voltage, or said electric stimulation is delivered as pulsed voltage.

26. The method of claim 12, wherein said electric stimulation is delivered at a frequency of about 0.1 Hz to about 2500 Hz, said electric stimulation is delivered at a pulse width of about 10 μsec to about 10 sec, said electric stimulation is delivered at a voltage of about 1 V to about 40 V, and said electric stimulation is delivered at a current of about 100 μA to about 20 mA.

27. The method of claim 12, wherein said electrostimulation device is further configured to deliver electrical stimulation to one or more specific brain tissue volumes.

* * * * *